United States Patent [19]

Johnson

[11] Patent Number: 5,591,182
[45] Date of Patent: Jan. 7, 1997

[54] ATRAUMATIC SURGICAL CLAMPING INSTRUMENT

[75] Inventor: Gary M. Johnson, Mission Viejo, Calif.

[73] Assignee: Applied Medical Resources Corporation, Laguna Hills, Calif.

[21] Appl. No.: 324,418

[22] Filed: Oct. 17, 1994

[51] Int. Cl.⁶ ................................................. A61B 17/00
[52] U.S. Cl. ........................................... 606/151; 606/207
[58] Field of Search ........................ 606/151, 157, 606/158, 174, 191, 192, 205, 207, 120

[56] References Cited

U.S. PATENT DOCUMENTS

| | | |
|---|---|---|
| 1,556,755 | 10/1925 | Burman . |
| 2,743,726 | 5/1956 | Grieshaber . |
| 3,515,139 | 6/1970 | Mallina . |
| 3,746,002 | 7/1978 | Haller . |
| 4,120,302 | 10/1978 | Ziegler . |
| 4,499,798 | 2/1985 | Miskiewicz . |
| 4,727,876 | 3/1988 | Porat et al. . |
| 4,821,719 | 4/1989 | Fogarty . |
| 4,834,090 | 5/1989 | Moore . |
| 4,988,355 | 1/1991 | Leveen et al. ........................ 606/158 |
| 5,009,657 | 4/1991 | Cotey et al. . |
| 5,242,458 | 9/1993 | Bendel et al. ........................ 606/147 |
| 5,250,072 | 10/1993 | Jain . |
| 5,258,005 | 11/1993 | Christian ........................... 606/205 |
| 5,282,812 | 2/1994 | Suarez, Jr. . |

*Primary Examiner*—Guy V. Tucker
*Attorney, Agent, or Firm*—Richard L. Myers

[57] ABSTRACT

A surgical clamping device includes a first jaw and a second jaw movable relative to the first jaw between the proximal position and a spaced position. The first jaw has a supporting surface facing toward the second jaw and an opposing surface facing away from the second jaw. An insert is removably mountable in an operative position on the first jaw and includes an insert base having a central wall and a pair of side walls which form a channel configured to receive the first jaw. An elastomeric material forms a pad on the central wall facing the second jaw while the side walls extend away from the second jaw. Holes in the central wall increase the thickness of the pad without increasing the profile of the insert. A detent mechanism extends laterally of the first jaw between the supporting surface and the opposing surface of the first jaw without interfering with the structural integrity of the clamping device.

18 Claims, 3 Drawing Sheets

ATRAUMATIC SURGICAL CLAMPING INSTRUMENT

BACKGROUND OF THE INVENTION

1. Field of the Invention

This invention relates generally to surgical grasping, retracting and occluding devices having opposing jaws, and more specifically to such devices which are provided with atraumatic inserts which extend in opposing relationship along the jaws.

2. Discussion of the Prior Art

Clamps and clips have been used in surgical procedures to engage and release various body structures such as organs and conduits. Such instruments are commonly referred to by the function that they perform once the organ has been engaged. Thus, the prior art includes graspers which engage the organ, retractors which are used to move the organ to a different location, and occluders which are used to close body conduits. All of these instruments include opposing jaws which are movable relative to each other between a proximate position wherein the organ is engaged, and a spaced position wherein the organ is released.

Where the organ is particularly fragile, these clamping devices have been provided with atraumatic inserts which are mountable on the jaws of the device, and include a compressible elastomeric material which softens the grip on the organ. Unfortunately, these inserts have added greatly to the profile of these devices. Where such devices have been used in open surgery, spacial limitations have easily accommodated the relatively large profile. However, in more confined surgeries, such as laparoscopic procedures, the relatively high profiles have not been tolerable.

One such laparoscopic surgery involves the removal of the gall bladder. When this organ is diseased, use of a grasper or retractor without inserts can result in tearing the organ. This not only releases toxic bile into the abdominal cavity, but also can release gall stones into the pneumoperitoneum. In either case, the procedure is dramatically complicated simply because soft jaw inserts producing a high clamp profile which could not be used in this type of surgery.

The high clamp profiles have resulted not only from the configuration of the inserts, but also from the structure relied on for attaching these inserts to the associated jaws. In the latter regard, holes have been drilled into the supporting surface of the associated jaw. Oversized projections on the insert have been forced into these holes to maintain the insert and jaw in a fixed relationship. Unfortunately, drilling a hole into the supporting surface of the jaw has substantially weakened the jaw particularly in the direction of closure which extends between the jaws. To overcome this weakness, an additional depth of material has been required along the plane of closure to add structural integrity to the jaws.

The inserts of the prior art have included an insert base which generally extends along the direction of closure away from the supporting surface. Side walls of the insert base have extended toward the opposing jaw to further increase the profile of the clamping device.

A third element adding to this profile is the depth of the elastomeric material which is relied on for the atraumatic feature of the insert. This depth of elastomeric material has been accommodated almost totally in the space extending between the insert base and the second jaw.

Each of these structural limitations has added to the profile of the clamping devices of the past. Where these features have appeared in combination, atraumatic clamping has only been possible in open surgeries.

SUMMARY OF THE INVENTION

In accordance with the present invention, surgical clamping devices can now be provided with a relatively low profile facilitating their use in procedures offering limited space, such as laparoscopic surgeries. An insert is provide which includes an insert base formed with a center wall and a pair of spaced opposing side walls. These three walls form a longitudinal channel in the insert base which is sized and configured to receive the associated jaw of the clamping device. The elastomeric material is disposed on the side of the center wall opposite the side walls.

With the side walls of the base insert extending generally parallel to the plane of closure, the insert is structurally inhibited from bending in the direction of closure. However, with the side walls extending away from the second jaw, this structural integrity is achieved without a sacrifice to the profile of the insert.

The center wall of the insert base can also be formed with holes so that the elastic material extends through the center wall to the supporting surface of the jaw. This accommodates a greater thickness of the elastomeric material, thereby adding to the atraumatic characteristics of the insert. This feature is accomplished without a sacrifice to the profile, since the depth of the elastomeric material is accommodated without regard for the thickness of the center wall.

Removable attachment of the insert to the jaw is facilitated by a detent mechanism which extends between the side walls of the insert and the side surfaces of the associated jaw. Placing the detent in this region, enables the supporting surface of the jaw to be maintained in a continuous, unbroken surface which enhances the strength of the jaw. Where the detent attachment mechanism includes a projection and an associated recess, the recess can be formed in the side of the jaw leaving the jaw with an "I-beam" construction which maximizes the strength of the jaw in the plane of closure.

All of these features can be combined to enhance the structural integrity of both the jaw and the insert while at the same time significantly reducing the profile of the clamping device.

These and other features and advantages of the invention will become more apparent with the description of preferred embodiments and the best mode of the invention, and reference to the associated drawings.

DESCRIPTION OF THE DRAWINGS

FIG. 4b is a top plan view of the jaw illustrated in FIG. 4a;

FIG. 4c is a cross section view taken along lines 4c—4c of FIG. 4a;

FIG. 5b is an axial cross section view taken along lines 5b—5b of FIG. 5a;

DESCRIPTION OF PREFERRED EMBODIMENTS AND BEST MODE OF THE INVENTION

Figure 1:
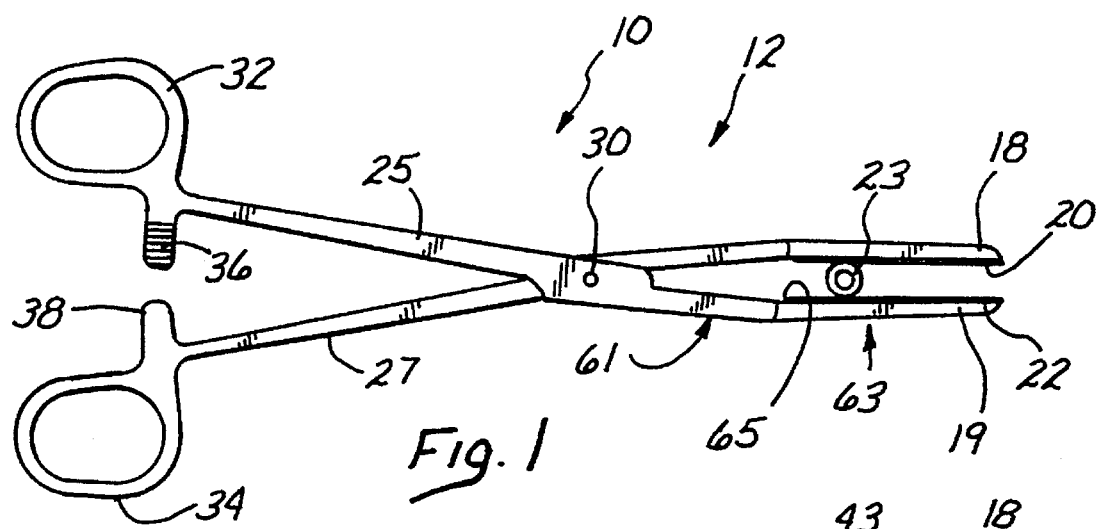
FIG. 1 is a side elevation view of a clamping device having a pair of opposing jaws and more specifically an atraumatic occluding device of the present invention.
Figure 2:
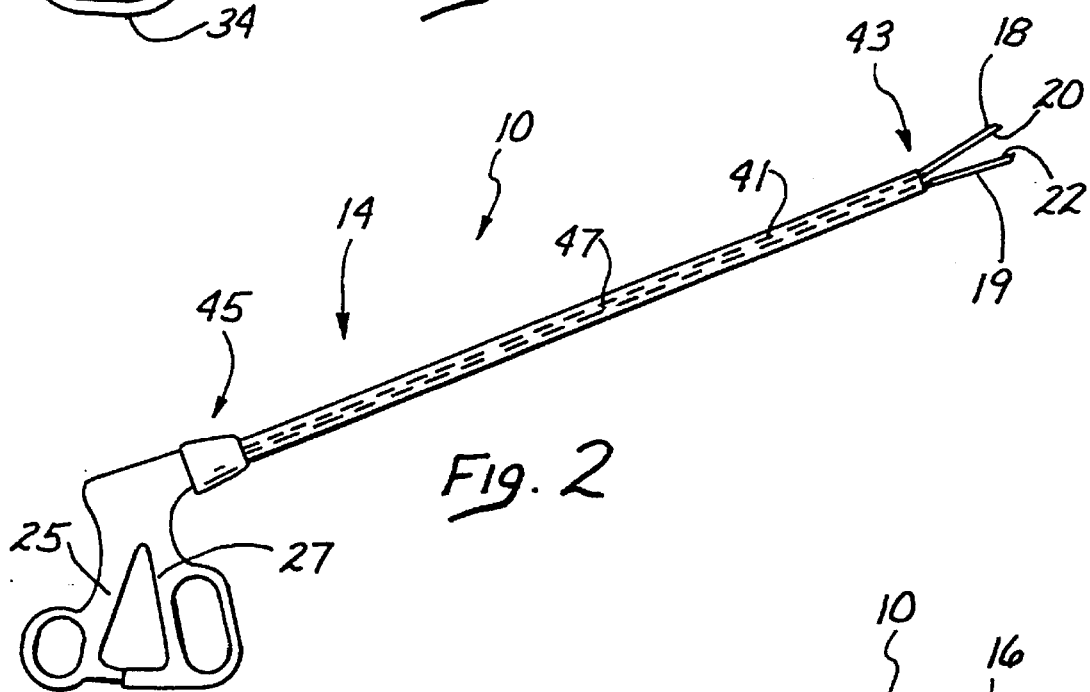
FIG. 2 is a side elevation view of a laparoscopic grasper in an additional embodiment of the invention.
Figure 3:
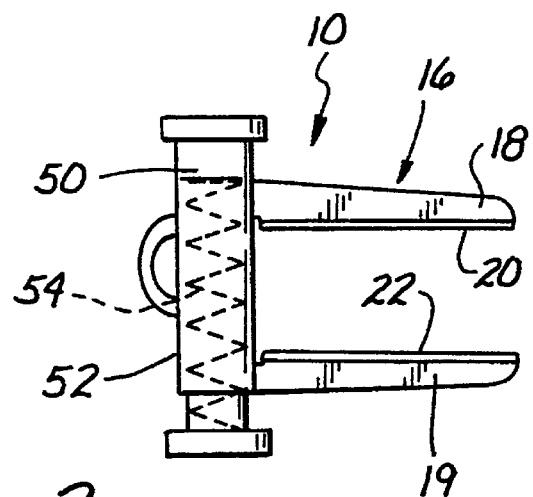
FIG. 3 is a side elevation view of a vascular clip in a further embodiment of the invention.

A clamping device is illustrated in FIGS. 1, 2 and 3 and designated generally by the reference numeral 10. In FIG. 1, the device 10 is in the form of a vessel occluder 12. A similar device 10 is illustrated in FIG. 2 in the form of a laparoscopic retractor 14. Still a further clamping device 10 is illustrated in FIG. 3 in the form of a vessel clip 16.

These clamping devices 10 are similar in that they each include a pair of opposing jaws 18 and 19 with an associated insert 20, 22. These jaws 18, 19 and inserts 20, 22 are movable between a proximate position and a spaced position. In the proximate position, the jaws 18, 19 and inserts 20, 22 are closely spaced or contacting to engage a body structure such as an organ or a conduit, for example a vessel 23 as illustrated in FIG. 1. In the released position, the jaws 18, 19 and inserts 20, 22 are spaced, thereby permitting release of the body organ, such as the vessel 23.

The clamping device 10 represented by the occluder 12, retractor 14, and clip 16, are dissimilar in their mechanism for moving the jaws 18 and 19 between the proximate and spaced position. In the case of the occluder 12 illustrated in FIG. 1, a pair of crossing handles 25 and 27 pivot at a fulcrum pin 30 and terminate at respective thumb loops 32 and 34. A pair of ratchet tabs 36 and 38 associated with the respective handles 25 and 27, provide means for locking the jaws 18 and 19 in a preferred relationship. In this embodiment, the means for moving the jaws 18, 19 functions as a scissors.

In the case of the laparoscopic retractor 14, the means for moving the jaws 18, 19 includes a longitudinal tube 41 having a distal end 43 and a proximal end 45. The jaws 18, 19 are disposed at the distal end 43, while the handles 25, 27 are disposed at the proximal end 45. One of the jaws 18, 19 is attached to a shaft 47 which is axially movable within the longitudinal tube 41. At the proximal end 45, the shaft 47 is attached to and movable with one of the handles 25 and 27. Operation of the handles 25 and 27 in a scissors fashion, results in movement of the jaws 18 and 19 between the proximate and spaced positions.

The vessel clip 16 illustrated in FIG. 3 can include similar jaws 18, 19. However in this embodiment, the means for moving the jaws 18, 19 includes telescoping cylinders 50, 52 each of which is attached to an associated one of the jaws 18, 19. The telescoping movement of these cylinders 50, 52 against the bias of a spring 54 results in relative movement of the jaws 18, 19.

The remainder of the disclosure will be presented with reference to the vessel occluder 12 of FIG. 1. However, it will be apparent that the invention is equally applicable to retractors, clips, graspers, and other clamping devices 10 which have opposing jaws. This is without regard to the particular mechanism which is relied on for movement of those opposing jaws between the proximate and spaced positions. The disclosure will also be referenced to a single one of the jaws 18, 19 realizing that in a typical embodiment, the opposing jaw 18 may have a similar configuration.

The dimension of the jaw structure which is of particular interest to the present invention is the dimension which occurs in a direction of closure that extends between adjacent points on the opposing jaws 18 and 19. When the jaws 18, 19 are straight, this direction of closure extends along a plane 56 which is illustrated in FIG. 4b as a line. It will be understood that if the jaws 18, 19 are curved, this direction of closure will also be curved, but nevertheless will extend between adjacent points on the opposing jaws 18 and 19.

Referring now to the preferred embodiment of FIG. 1, it can be seen that the jaw 19 may include a relatively thick section 61 and a relative thin section 63. In the side view of FIG. 4a, a distally facing shoulder 65 separates the two sections 61 and 63. In the plan view of FIG. 4b, distally facing shoulders 67 and 70 separate the two sections 61 and 63. Thus it can be seen that in this embodiment, the relatively thin section 63 is reduced in both height and width with respect to the thick section 61.

Figure 4A:
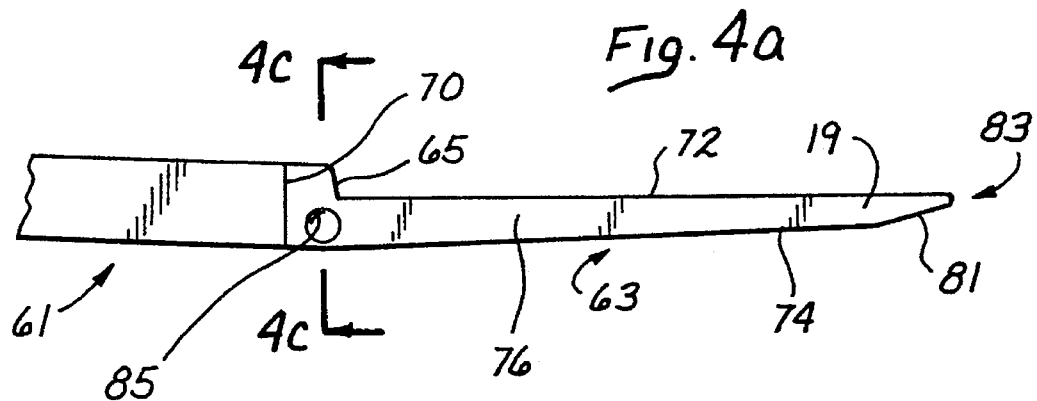
FIG. 4a is an elevation view of one of the jaws associated with the clamping device of the present invention.
Figure 4B:
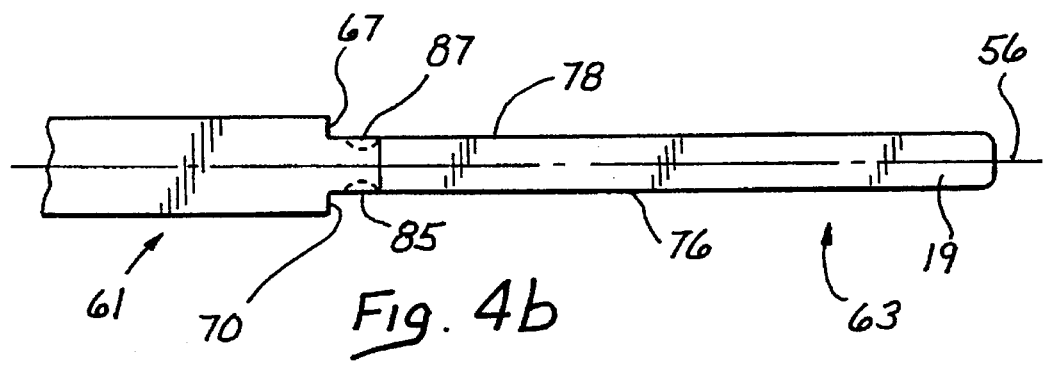
Figure 4C:
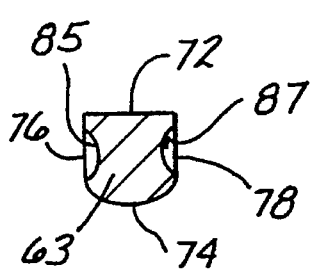

As best illustrated in FIG. 4a, the thin section 63 is characterized by a longitudinal configuration with a top supporting surface 72 and a bottom opposing surface 74. Side surfaces 76 and 78 are best shown in the cross-sectional view of FIG. 4c.

At the distal tip of the jaw 19, a beveled or otherwise reduced surface 81 extends from the supporting surface 72 to the opposing surface 74 in a proximal direction. Thus, the distal tip of the jaw 19 tends to form a projection 83 where the surface 81 intersects the supporting surface 72.

At least one and preferably two recesses 85 and 87 can be formed along the side surfaces 76 and 78 in general proximity to the shoulders 65–70, in the manner described in greater detail below. These recesses 85 and 87 function as part of a system for removably attaching the insert 22 to the jaw 19. Importantly, the supporting surface 72 and opposing surface 74 remain continuous and unbroken in this embodiment. Additionally, the recesses can be placed as shown in the relatively thick section 61. As a result, the strength of the jaw in the plane of closure 56 remains unaffected by the recesses 85 and 87 in the side wall 76 and 78, respectively. The resulting "I-beam" cross section, well-known for its resistance to bending, is best illustrated in the cross sectional view of FIG. 4c.

Figure 5B:
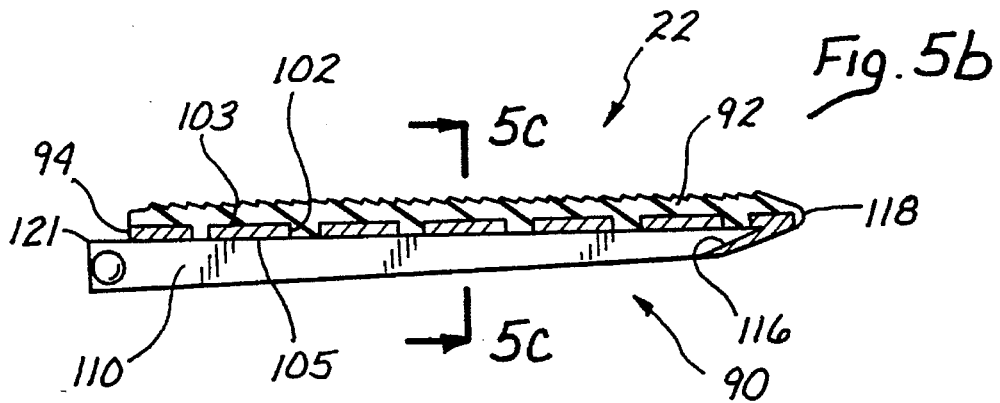
Figure 5C:
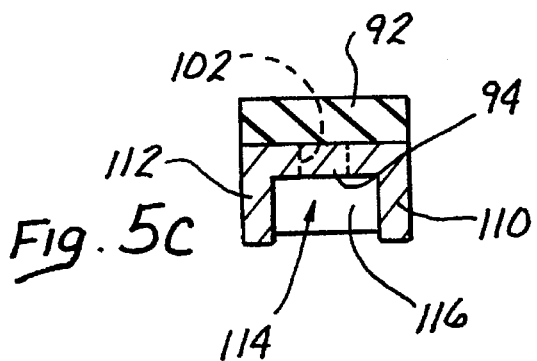
FIG. 5c is a radial cross section view taken along lines 5c—5c of FIG. 5b.
Figure 5A:
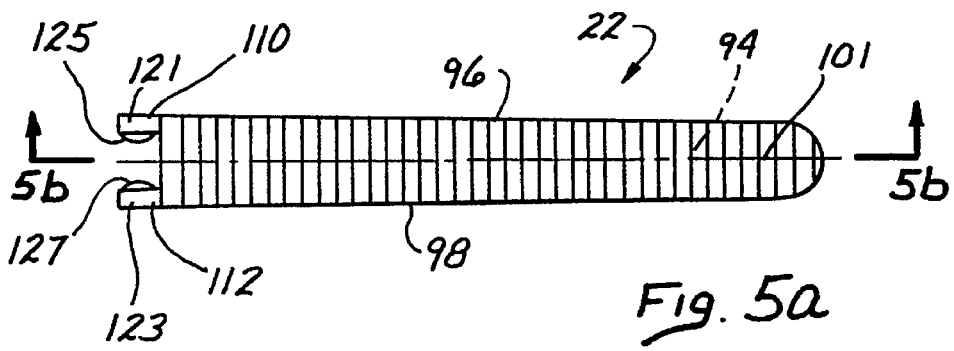
FIG. 5a is a top plan view of a jaw insert associated with the present invention.
Figure 6A:
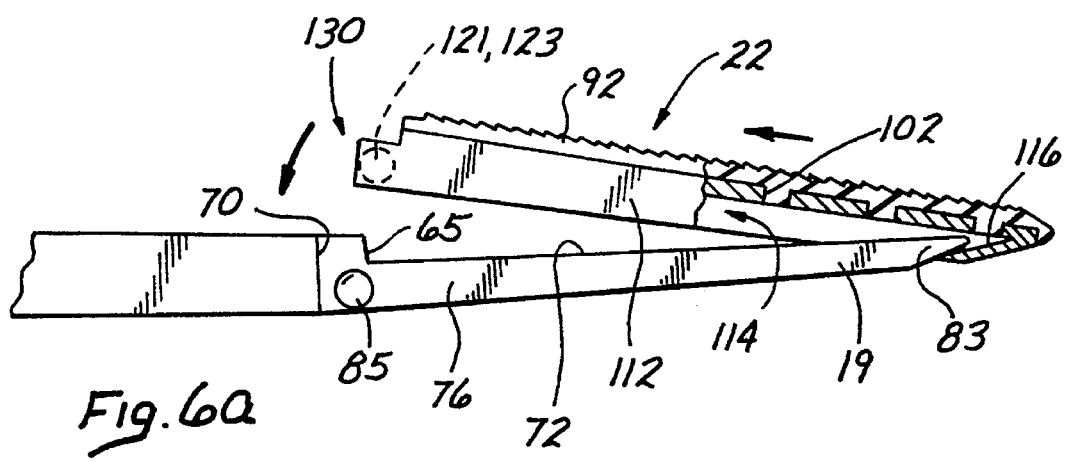
FIG. 6a is a side elevation view illustrating an insert being mounted on a clamping jaw associated with the present invention.
Figure 6B:
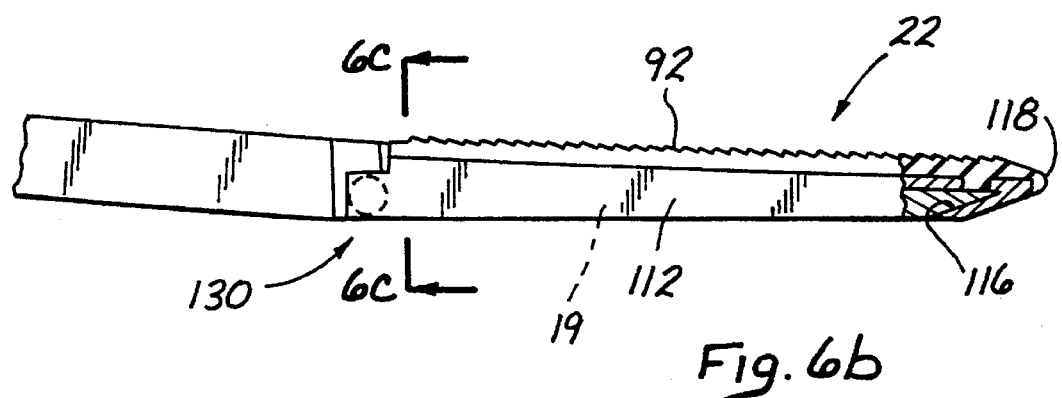
FIG. 6b is a side elevation view of the insert mounted in an operative position on the associated jaw.
Figure 6C:
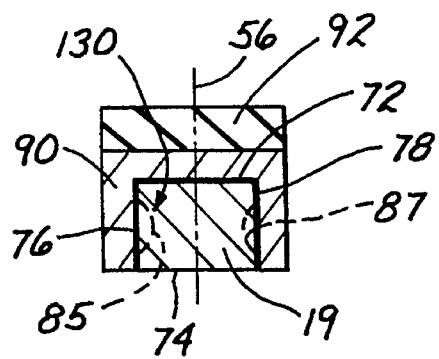
FIG. 6c is a cross section view taken along lines 6c—6c of FIG. 1 and FIG. 6b.

A preferred embodiment of the insert 22 is illustrated in FIGS. 5 and 6. The insert 22 includes an insert base 90, typically formed from a hard plastic such as polypropylene, and a pad 92, typically formed from an elastomeric material such as latex or thermoplastic elastomer. In a preferred embodiment, the insert base 90 includes a center wall 94 which extends longitudinally between edges 96 and 98. A center line 101 extends intermediate the edges 96 and 98 and is disposed in the plane of closure 56 when the insert 22 is operatively disposed on the jaw 19. The center wall 94 has an upwardly facing surface 103 and a downwardly facing surface 105.

A pair of side walls 110 and 112 are also included in the insert base 90. These side walls 110 and 112 extend in a common direction, downwardly in FIG. 5b, from the respective edges 96 and 98 of the center wall 94. Thus, the side walls 110 and 112 are spaced from each other and form with the center wall 94 a channel 114 which extends along the length of the insert 22. This channel 114 is best illustrated in FIG. 5c. At the distal end of the insert base 90, the channel 114 is closed and forms an undercut 116.

In the illustrated embodiment, the center wall 94 is provided with holes 102 along the center line 101. These holes 102 extend at least a portion of the distance from the upwardly facing surface 103 to the downwardly facing surface 105. In the preferred embodiment illustrated, the holes 102 extend entirely through the center wall 94.

It is the holes 102 which facilitate several functions associated with the elastomeric pad 92 of the present invention. In a preferred method of manufacture, this pad 92 is generally molded onto the upwardly facing surface 103. Since this surface is broken by the holes 102, a portion of the elastomeric material forming the pad 92 flows into the holes 102 thereby assisting in anchoring the elastomeric pad 92 to the base 90 of the insert 22.

The holes 102 also contribute to the elastomeric characteristic of the pad 92. In the illustrated embodiment, the thickness of the elastomeric pad 92 is locally increased by the depth of the holes 102. This additional thickness provides an increased degree of softness for the insert 22 thereby contributing to the atraumatic characteristics of the clamping device 10.

At the distal end of the insert 22, the elastomeric material 92 can extend beyond the insert base 90 to form a soft nose 118 at the distal tip of the insert 22 and the distal end of the clamping device 10.

At the proximal end of the insert base 90, the side walls 110 and 112 can extend beyond the center wall 94 to form respective flanges 121 and 123. Inwardly facing projections 125 and 127 extend toward each other from the inner surfaces of the respective flanges 121 and 123. These projections 125 and 127, which take the form of spheres in a preferred embodiment, are part of a detent mechanism 130 which aids in attaching the insert 22 to the jaw 19.

The mounting of the insert 22 on the associated jaw 19 is preferably accomplished as illustrated in FIG. 6a. Initially, the projection 83 at the end of the jaw 19 is seated in the undercut 116 at the end of the channel 114 of the insert 22. The insert 22 is then rotated downwardly until the detent mechanism 130 is actuated to mount the insert 22 in a snap fit relationship on the jaw 19. Initially the projections 125, 127 cause the flanges 121, 123 to spread as they slide along the associated side surfaces 76, 78 of the jaw 19. When these projections 125, 127 reach the recesses 85 and 87, the flanges 121, 123 snap inwardly to seat the jaw 19 into the channel 114 of the insert 22.

The features associated with this construction are of particular interest as they result in a low profile for the inserts 20, 22 and associated jaws 18, 19. This low profile is achieved without any sacrifice in the strength or integrity of the resulting structure.

It will first be noted that the center wall 94 of the insert 22 can be relatively thin in profile since the side walls 110, 112 can be relied on to maintain the structural rigidity of the base 90. And while the side walls 110, 112 maintain the structural integrity of the insert 22, they are positioned to extend away from the elastomeric pad 92. Accordingly, they make no contribution to the thickness of the jaw/insert combination along the plane of closure 56.

This profile is further reduced by permitting the elastomeric material of the pad 92 to extend through the center wall 94 to the supporting surface 72 of the jaw 19. Given this additional thickness for the pad 92, substantial elastomeric properties can be achieved with only a thin layer of the pad 92 extending beyond the upwardly facing surface 103 of the center wall 94.

Formation of the detent mechanism 130 between the side walls 110, 112 and the associated side surfaces 76, 78 of the jaw 19 facilitates attachment of the insert 22 to the jaw 19, again without sacrificing the structural integrity of the jaw 19. With this detent mechanism 130, additional material that might add to the profile, is not needed to enhance the structure of the jaw 19.

The resulting low profile associated with the clamping device 10 will be particularly appreciated in those surgical environments which do not provide an abundance of space. Particularly in those procedures associated with laparoscopic surgery, the clamping device 10 such as the retractor 14 illustrated in FIG. 2 can be provided with the low profile inserts 20 and 22 in order to provide atraumatic clamping.

It will be apparent that various modifications to the foregoing embodiments can be made to achieve other advantages associated with the invention. For example, the detent mechanism 130 can be modified so that the projections 125, 127 and recesses, 85, 87 are reversed. This would add additional material to the jaw 19 even further enhancing the structural integrity of this element. Other forms of projections and recesses can be used to attach the inserts 20, 22 to the associated jaws 18, 19. As long as any recesses, such as the recesses 85 and 87, are formed along the side surfaces 76, 78, the "I-beam" cross section of the jaw 19 will not be sacrificed.

The materials associated with the various elements described can also be modified. In general, the base 90 of the insert 22 can be formed from any material providing some degree of rigidity for the insert 22 as well as also a degree of flexibility as required by the attachment mechanism, such as the detent mechanism 130. It will be apparent that the elastomeric material forming the pad 92 can also vary considerably. The elastomeric properties of course contribute to the atraumatic characteristics of the inserts 20, 22, but other materials such as fibers can also achieve this advantage. The pad 92 can also be molded to any base, such as the base 90, having a profile which facilitates use of the clamping device 10 in a particular environment.

The configuration of the center wall 94 of the insert 22 can also vary considerably. Since this wall 94 is relied on primarily to support the pad 92 and to form the channel 114 with the side walls 110, 112, its shape and thickness can vary significantly with different embodiments. Also, the formation of the holes 102 in various sizes and shapes may enhance the atraumatic and low profile characteristics of a particular construction.

Given these wide variations, which are all within the scope of this concept, one is cautioned not to restrict the invention to the embodiments which have been specifically disclosed and illustrated, but rather encouraged to determine the scope of the invention only with reference to the following claims.

I claim:

1. A surgical clamping device for releasably engaging a body structure, including:

a first jaw;

a second jaw disposed in opposing relationship with the first jaw and movable relative to the first jaw between a first position wherein the first and second jaws have a proximate relationship to engage the body structure, and a second position wherein the first and second jaws have a spaced relationship to release the body structure;

the first jaw having a supporting surface facing generally toward the second jaw and an opposing surface facing generally away from the second jaw;

an insert removably mountable in operative disposition on the first jaw;

an insert base included in the insert, the base being sized and configured for disposition on the supporting surface of the first jaw;

an elastomeric material included in the insert and carried by the insert base;

means for attaching the insert base to the first jaw; and the attachment means engaging the first jaw and the insert base proximally of the supporting surface of the first jaw, without contacting said supporting surface, when the insert is operatively disposed on the first jaw.

2. A surgical clamping device for releasably engaging a body structure, including:

a first jaw;

a second jaw disposed in opposing relationship with the first jaw and movable relative to the first jaw between a first position wherein the first and second jaws have a proximate relationship to engage the body structure, and a second position wherein the first and second jaws have a spaced relationship to release the body structure;

the first jaw having a supporting surface facing generally toward the second jaw and an opposing surface facing generally away from the second jaw;

an insert removably mountable in operative disposition on the first jaw;

an insert base included in the insert, the base being sized and configured for disposition on the supporting surface of the first jaw and including a center wall having a first surface and a second surface disposed in opposition to the first surface, the first surface contacting the supporting surface of the first jaw when the insert is operatively disposed on the first jaw;

portions of the insert base defining at least one hole extending at least a portion of the distance from the second surface of the insert base toward the first surface of the insert base;

an elastomeric material included in the insert and carried by the insert base, portions of the elastomeric material extending into the at least one hole in the insert base;

means for attaching the insert base to the first jaw; and the attachment means engaging the first jaw and the insert base when the insert is operatively disposed on the first jaw.

3. The device recited in claim 2 wherein:

the at least one hole extends the entire distance from the second surface of the insert base to the first surface of the insert base; and the portions of the elastomeric material extend through the at least one hole into contact with the supporting surface of the first jaw when the insert is operatively disposed on the first jaw.

4. The device recited in claim 3 wherein the insert base further comprises:

a first side wall extending from the center wall;

a second side wall spaced from the first side wall and extending from the center wall in the same direction as the first side wall; and the center wall forming with the first side wall and the second side wall a longitudinal channel sized and configured to receive the first jaw of the clamping device.

5. The device recited in claim 4 wherein the attachment means is positioned between the first jaw and at least one of the first side wall and the second side wall of the insert.

6. The device recited in claim 5 wherein the attachment means comprises a detent extending laterally between the first jaw and the at least one of the first side wall and the second side wall.

7. The device recited in claim 6 wherein the detent includes a projection extending from one of the first jaw and the at least one of the side walls, and a recess formed in the other of the first jaw and the at least one side wall, the projection and the recess being positioned for alignment with each other when the insert is disposed in the operative position on the first jaw.

8. A surgical clamping device for releasably engaging a body structure, including:

a first jaw having a supporting surface and a pair of opposing side surfaces;

a second jaw disposed in opposing relationship with the first jaw and movable relative to the first jaw between a proximate position wherein the first jaw and the second jaw have a proximate relationship to engage the body structure, and a spaced position to release the body structure;

at least one of the first jaw and second jaw being movable in a plane between the proximate position and the spaced position;

an insert removably mounted in an operative position on the first jaw;

an insert base included in the insert, the base being sized and configured for disposition on the first jaw;

a center wall included in the insert base and extending along the supporting surface of the first jaw when the insert is in the operative position on the first jaw;

a pair of side walls included in the insert base and extending along the side surfaces of the first jaw when the insert is in the operative position on the first jaw;

an elastomeric pad disposed along the center wall of the insert base;

at least one detent disposed between the side walls of the insert and the side surfaces of the first jaw.

9. The device recited in claim 8 wherein the side walls of the insert base extend generally parallel to the particular plane of the at least one first jaw and second jaw to resist bending of the insert in the particular plane.

10. The device recited in claim 8 further comprising:

portions of the center wall defining at least one hole extending through the center wall; and portions of the elastomeric pad extending through the at least one hole in the center wall into contact with the supporting surface of the first jaw.

11. The device recited in claim 8 wherein the supporting surface of the first jaw is continuous.

12. The device recited in claim 8 wherein the center wall of the insert base and the side walls of the insert base form a longitudinal channel sized and configured to receive the first jaw of the clamping device.

13. The device recited in claim 8 wherein the detent includes:

a projection extending laterally from one of the side walls of the insert base;

portions of the first jaw defining a recess in one of the side surfaces of the first jaw; and the projection of the one side wall extends into the recess of the first jaw when the insert is in the operative position on the first jaw.

14. A surgical clamping device for releasibly engaging a body structure, including:

a first jaw having a supporting surface and a pair of opposing side surfaces;

a second jaw disposed in opposing relationship with the first jaw and movable relative to the first jaw between a proximal position wherein the first jaw and the second jaw have a proximate relationship to engage the body structure, and a spaced position wherein the first jaw and the second jaw have a spaced relationship to release the body structure;

at least one of the first jaw and second jaw being movable between the proximal position and the spaced position;

an insert removably mountable in an operative position on the first jaw;

an insert base included in the insert and disposed in contact with the supporting surface of the first jaw, portions of the insert base defining at least one hole extending through the insert base; and an elastomeric pad included in the insert and disposed on the insert base with portions of the elastomeric pad extending through the at least one hole in the insert base into contact with the supporting surface of the first jaw.

15. The device recited in claim 14 wherein the insert base comprises:

a center wall of the insert base extending along the supporting surface of the first jaw;

a pair of side walls spaced from each other and extending along the center wall; and the center wall and the pair of side walls forming a longitudinal channel sized and configured to receive the first jaw of the device.

16. The device recited in claim 15 wherein:

the first jaw and the second jaw are disposed in a plane;

the supporting surface of the first jaw faces the second jaw;

the side walls of the insert base extend generally parallel to said plane to inhibit bending of the insert along the plane.

17. The device recited in claim 15 wherein the side walls of the insert base extend from the center wall away from the second jaw.

18. The device recited in claim 14 wherein the supporting surface of the first jaw is continuous.

* * * * *